US008691268B2

(12) United States Patent
Weimann

(10) Patent No.: US 8,691,268 B2
(45) Date of Patent: Apr. 8, 2014

(54) TRANSDERMAL DELIVERY USING ENCAPSULATED AGENT RELEASED BY ULTRASOUND AND/OR HEAT

(75) Inventor: Ludwig J. Weimann, Burlington, VT (US)

(73) Assignee: Ultra-Sonic Technologies, L.L.C., St. Albans, VT (US)

( * ) Notice: Subject to any disclaimer, the term of this patent is extended or adjusted under 35 U.S.C. 154(b) by 80 days.

(21) Appl. No.: 12/883,153

(22) Filed: Sep. 15, 2010

(65) Prior Publication Data

US 2011/0004150 A1 Jan. 6, 2011

Related U.S. Application Data

(62) Division of application No. 10/541,001, filed as application No. PCT/US03/41850 on Dec. 31, 2003, now abandoned.

(60) Provisional application No. 60/437,541, filed on Dec. 31, 2002.

(51) Int. Cl.

| A61K 9/70 | (2006.01) |
|---|---|
| A61K 38/28 | (2006.01) |
| A61N 1/30 | (2006.01) |
| A61K 9/00 | (2006.01) |
| A61M 37/00 | (2006.01) |

(52) U.S. Cl.
CPC .......... *A61K 9/0009* (2013.01); *A61K 9/7084* (2013.01); *A61K 9/7092* (2013.01); *A61K 9/0014* (2013.01); *A61M 37/00* (2013.01); *A61M 37/0092* (2013.01); *A61N 1/30* (2013.01)
USPC .............. 424/449; 424/448; 514/5.9; 604/20; 604/22

(58) Field of Classification Search
None
See application file for complete search history.

(56) References Cited

U.S. PATENT DOCUMENTS

| 3,242,051 | A | | 3/1966 | Hiestand et al. |
|---|---|---|---|---|
| 4,558,690 | A | | 12/1985 | Joyce |
| 4,787,888 | A | * | 11/1988 | Fox ................................ 604/20 |
| 4,830,355 | A | | 5/1989 | Jeschke |
| 5,019,034 | A | | 5/1991 | Weaver et al. |
| 5,190,766 | A | | 3/1993 | Ishihara |
| 5,224,927 | A | | 7/1993 | Tapper |
| 5,614,212 | A | | 3/1997 | D'Angelo et al. |
| 5,688,233 | A | | 11/1997 | Hofmann et al. |
| 5,733,572 | A | | 3/1998 | Unger et al. |
| 5,814,599 | A | | 9/1998 | Mitragotri et al. |

(Continued)

OTHER PUBLICATIONS

Frinking, P. J. A, et al. Ultrasonics (1998), 36; pp. 709-712.*

(Continued)

*Primary Examiner* — Kevin S Orwig

(74) *Attorney, Agent, or Firm* — Gerry J. Elman; Elman Technology Law, P.C.

(57) ABSTRACT

A method for delivery of substance through at least one dermal layer, by providing a substance in microcapsules at a predetermined size, within a medium (150) for holding the microcapsules; placing the medium for holding the microcapsules on a surface of a patch (100) adjacent the skin (320) of a human or animal; and applying energy (200) to the patch, the energy having a characteristic of disturbing the integrity of the microcapsules, thereby resulting in release of the substance from the microcapsules. The energy may be selectively applied to release the substance at desired times. The substance may be a drug or other active agent.

15 Claims, 4 Drawing Sheets

(56) References Cited

U.S. PATENT DOCUMENTS

| | | | |
|---|---|---|---|
| 5,947,921 A | | 9/1999 | Johnson et al. |
| 6,041,253 A | * | 3/2000 | Kost et al. ............ 604/20 |
| 6,048,545 A | * | 4/2000 | Keller et al. ............ 424/450 |
| 6,119,036 A | * | 9/2000 | Allen, Jr. ............ 604/20 |
| 6,190,315 B1 | * | 2/2001 | Kost et al. ............ 600/309 |
| 6,487,447 B1 | | 11/2002 | Weimann et al. |
| 2002/0055702 A1 | * | 5/2002 | Atala et al. ............ 604/20 |

OTHER PUBLICATIONS

Kunta Jr, Goskonda VR, Brotherton HO, Khan MA, Reddy IK; Effect of menthol and related terpenes on the percutaneous absorption of propranolol across excised hairless mouse skin; J Pharm Sci. Dec. 1997; 86(12): 1369-73.

Ken Ishihara, Akira Kitabatake, Jun Tanouchi, Kenshi Fujii, Masaaki Uematsu, Yutaka Yoshida, Takenobu Kamada, Tatsuhiro Tamura, Kunihiro Chihara, Kimisuke Shirae; New Approach to Noninvasive Manometry Based on Pressure Dependent Resonant Shift of Elastic Microcapsules in Ultrasonic Frequency Characteristics; Japanese J. Appl. Phys. 27 (1988) Supplement 27-1 pp. 125-127; Proc. 8th Symp. Ultrasonic Electronics, Tokyo, 1987.

Turner NG, Ferry L, Price M, Cullander C, Guy RH; Iontophoresis of poly-L-lysines: the role of molecular weight?; Pharm Res. Oct. 1997; 14(10):1322-31.

Turner NG, Ferry L, Price M, Cullander C, Guy RH; Iontophoresis of poly-L-lysines: the role of molecular weight?; Erratum; Pharm Res. Mar. 1998; 15(3):504-7.

* cited by examiner

TRANSDERMAL DELIVERY USING ENCAPSULATED AGENT RELEASED BY ULTRASOUND AND/OR HEAT

CROSS REFERENCE TO RELATED APPLICATIONS

This application is a Divisional Application of co-pending U.S. patent Non-Provisional application Ser. No. 10/541,001, filed Jun. 28, 2005, which is a National Stage entry of International Patent Application, Serial Number PCT/US2003/041850, filed Dec. 31, 2003, which claims benefit of U.S. Provisional Patent Application 60/437,541, filed Dec. 31, 2002. The entire disclosures of each of the aforementioned applications are incorporated herein by reference.

TECHNICAL FIELD

This invention relates to transdermal delivery of active substances to the body, and more specifically to a system for augmenting transdermal delivery with ultrasonic and/or heat energy.

The present invention is useful for delivery of drugs, medications, cosmetic substances and other materials through at least one epidermal layer. To describe such delivery of substances, the conventional term "drug delivery" will sometimes be used. Unless a specific substance is described, the term "active substance" is intended to mean any substance for which transdermal or subdermal delivery is to be accomplished. A drug to be delivered would therefore be an "active substance." The individual (human or animal) to whose skin the active substance is to be delivered is referred to sometimes as a "patient" and sometimes as a "user" of the inventive patch; these are intended to be interchangeable terms as used herein.

BACKGROUND ART

Drug delivery, and drugs incorporating drug delivery systems, are gaining increased interest. New drug delivery systems, including nasal sprays, extended-release oral formulations, topical creams, transdermal patches and inhalational compounds have the capacity to expand the convenience and usefulness of therapeutic agents, e.g. peptides. Conventionally, most of these compounds have been either administered by injection only or abandoned because of poor bioavailability and/or solubility. Novel drug delivery technologies offer new capabilities to revive the market potential by unleashing the therapeutic capabilities of these compounds, providing new solutions to old problems.

The transdermal administration of drugs is becoming increasingly accepted as a preferred mode of delivery. Transdermal delivery of drugs provides many advantages over conventional oral administration, including convenience, non-interrupted therapy, improved patient compliance, reversibility of treatment (by removal of the system from the skin), elimination of the "hepatic first pass" effect, a higher degree of control over blood concentration of any particular drug, and a consequent reduction of side effects.

Transdermal delivery of drugs requires transport of the drug molecules through the stratum corneum, i.e., the outermost layer of the skin. The stratum corneum ("SC") provides a formidable chemical barrier to any chemical entering the body, and only small molecules, with molecular weights less than 500 Daltons ("Da"), can passively diffuse through the SC at rates that enable therapeutic effects. (A Dalton is a unit of molecular weight as compared to the hydrogen atom.)

U.S. Pat. No. 5,733,572, to Unger, et al., describes compositions comprising gas and/or gaseous precursor filled microspheres, which include an active ingredient for application to tissue of a patient. The gas in the microspheres may serve to prevent oxidation and other forms of degradation of active ingredients, such as labile drugs, bioactive compounds and cosmetics, and the microspheres may be formed from, e.g., a biocompatible lipid or polymer. The lipid may be in the form of a monolayer or bilayer, and the mono- or bilayer lipids may be used to form a series of concentric mono- or bilayers. Thus, the lipid may be used to form a unilamellar liposome (comprised of one monolayer or bilayer lipid), an oligolamellar liposome (comprised of two or three monolayer or bilayer lipids) or a multilamellar liposome (comprised of more than three monolayer or bilayer lipids). Preferably, the biocompatible lipid is a phospholipid. The resultant gas or gaseous precursor filled microsphere composition, which often takes the form of a foam, provides a very creamy texture and skin penetration enhancing qualities for the topical or subcutaneous delivery of active ingredients. The active ingredients include drugs, especially peptides and other bioactive compounds, as well as cosmetics.

U.S. Pat. No. 4,558,690, to Joyce, "Method of Administration of Chemotherapy to Tumors," assigned to University of Scranton, describes an anticancer capsule comprising an antineoplastic agent encapsulated in a meltable polymer. Polyoctadecyl acrylate, a side-chain crystallizable polymer, is used as the meltable polymer. Once the composition has been delivered to the tumor, nonionizing radiation is used to locally heat the tumor and melt the capsule wall so that it disintegrates and permits the agent to be released by dissolution. Drug release does not occur via diffusion through the polymer.

U.S. Pat. No. 3,242,051, to Hiestand, et al., mentions polyvinyl stearate, another side-chain crystallizable polymer, as a precoating material in a two-step microencapsulation process. A described embodiment is a dose of 30 mg of methotrexate (A-methopterin) in the form of spherical microcapsules having an average of 200-800 microns diameter and a polymer of olystearyl acrylate encapsulating coating of an average thickness of 1-50 microns. This dose is injected into the tumor and released by a 30-60 minute irradiation of the tumor by 175-200 watts f RF non-ionizing radiation at a frequency of 13.56 megaHertz from a set of capacitive plates positioned on opposite sides of the impregnated tumors. The tumor temperature is elevated to a threshold temperature of 430° C., which is the melting point and release point of the encapsulated acrylic resin. The temperature of the rest of the organism outside the tumor remains at 390-400° C., which is below the release temperature of the resin.

U.S. Pat. No. 5,190,766, to Ishihara, et al., "Method of Controlling Drug Release by Resonant Sound Wave," assigned to Ken Ishihara (Hyogo, J P), describes a drug carrier carrying a drug, which is introduced to a diseased region of the living body while it is observed in the B mode echograms. The drug carrier is irradiated with an ultrasonic wave for strongly vibrating the drug carrier, thereby releasing the drug from the drug carrier for curing the diseased portion.

U.S. Pat. No. 5,614,212 to D'Angelo, et al., "Method of Transdermally Administering High Molecular Weight Drugs with a Polymer Skin Enhancer," assigned to International Medical Associates, Inc., describes a method of administering transdermally a high molecular weight drug by applying a polymer skin enhancer and a drug active to the skin of the patient. The drug active has a molecular weight of above 500 Daltons. The drug may be encapsulated or the drug solution may be partly encapsulated and partly free. The skin enhancer is preferably polyvinylpyrrolidone (PVP) and it is mixed at between 7 and 35% of the drug. A gelling agent may be optionally added at up to 20% by volume. The chemical system is preferably administered via a multidose transdermal drug patch assembly, which includes a drug-impervious support impressed to form a series of compartments. Each compartment is a reservoir for a unit dose of a drug active to be transdermally administered. The support is adhesively secured to the skin of a patient. Individual devices are provided for resealably enclosing the drug active in each of the reservoirs. The individual enclosing devices are removable to release the unit dose into contact with the skin of the patient and are actuable to control the transdermal absorption of the drug actives. The drug may also be administered in a cream.

Several methods have been proposed to facilitate transdermal delivery of molecules larger than 500 Da and increase the rate of drug delivery through the SC, including iontophoresis, electroporation, electroincorporation, sonophoresis and chemical enhancers.

The iontophoresis method utilizes low electric fields to drive drug molecules into the skin, as described in U.S. Pat. No. 5,224,927. However, iontophoresis is to greater extent limited to ionizable drugs and molecules and is ineffective for molecules with molecular weights greater than about 7,000 Da (i.e. 7 kDa), as described by N. G. Turner, et al., in Pharm. Research 14,1322-1331 (1997).

The electroporation and electroincorporation methods utilize high voltage electric pulses of 150 V that are directly applied to the skin, as described in U.S. Pat. No. 5,019,034. The electric pulses help open pores in the skin, thus allowing molecules above 7 kDa to pass through the skin. However, the use of high electric voltages poses safety problems and requires complicated equipment. Furthermore, the drugs need to be driven through the pores by some secondary means, e.g. as described in U.S. Pat. No. 5,688,233, which further complicates the application.

The sonophoresis method utilizes ultrasound and has been shown to be capable of delivering molecules up to 48 kDa, as described in U.S. Pat. No. 5,814,599 and U.S. Pat. No. 5,947,921.

However, the rate of delivery is extremely low, thus rendering it impractical. In the recently issued U.S. Pat. No. 6,487,447 of which the present applicant is a co-inventor, it was shown that transdermal passage of large polypeptide molecules can be accomplished using sonomacroporation.

Chemical enhancers such as unsaturated fatty acids, saturated fatty acids, their esters and terpenes can increase the flux through the SC for drugs having large molecular weights, such as estradiol, testosterone, and also polar drugs such as hydrochloride salts of basic drugs (e.g., propranolol.HCl), as described by J. R. Kunta, V. R. Goskonda, H. O. Brotherton, M. A. Khan, and I. K. Reddy., "Effect of Menthol and Related Terpenes on the Percutanious Absorption of Propranolol Across Excised Hairless Mouse Akin" J. Pharm. Sci. v.86, no. 12, 1369-1373 (1997), and in U.S. Pat. No. 5,947,921. However, chemical enhancers have serious formulation problems; they can cause skin irritations and unwanted plasticization of the transdermal patch adhesive used for their application; and their effectiveness depends upon the drug type and its application method.

Although transdermal systems have many advantages, most drugs are not amenable to this mode of administration due to their incompatibility with the carrier matrix or their instability in the carrier matrix environment.

Partitioning of a drug into the skin is dependent on the difference in the chemical potentials of the drug in the carrier matrix and the skin. Pressure-sensitive adhesives are relatively lipophilic, having solubility parameters very close to that of the skin. See, e.g. CRC Handbook of Solubility Parameters and Other Cohesion Parameters, $2^{nd}$ Ed., by A. F. M. Barton, especially sec. 2.2. The driving force of the drug from the carrier matrix to skin is directly proportional to the difference between the solubility parameters of the drug and the carrier matrix, and is inversely proportional to the difference between the solubility parameters of the drug and the skin.

Chemical enhancers such as unsaturated fatty acids, saturated fatty acids, their esters and terpenes, showed flux increases of drugs with larger molecular weights such as estradiol and testosterone, and also polar drugs such as hydrochloride salts of basic drugs (e.g., propranolol-HCl), as described in J. R. Kunta, et al, in J. Pharm. Sci. 86, 1369-1373 (1997), cited above. Practical use of chemical enhancers, however, is not yet very advanced due to serious formulating obstacles. Their enhancing properties are both vehicle- and drug-dependent; they also cause unwanted plasticization of the transdermal patch adhesive. Also liquid drugs, such as scopolamine or active agents such as nicotine, cause unwanted plasticization of the adhesive, affecting manufacturing efficiency due to problems with slitting and die cutting of the oozing laminates.

A number of drugs and active agents are not stable once dispersed in the matrix of an adhesive. For example, Vitamin C is unstable in aqueous solutions and is easy oxidizable in the matrix. Insulin, too, is very unstable in an adhesive matrix.

Presently marketed transdermal patches begin the delivery of a drug or other active substance to be delivered transdermally immediately upon being placed on the skin. In such a situation, the transdermal drug delivery kinetic profile is dependent on the fixed size of the patch and the fixed drug concentration in the matrix. Such patches cannot deliver a drug or other active substance to be delivered transdermally "as needed."

DISCLOSURE OF THE INVENTION

A transdermal patch system provides transdermal delivery of pharmaceutical and other active substances. The active substance is retained in microcapsules embedded in a monolithic matrix, and activation is achieved by the rupturing of the microcapsules upon application of energy as by ultrasound at a resonant frequency and/or heat. Partitioning of an active substance transdermally is enhanced by a difference in the chemical potentials of the substance in the carrier matrix and the skin. The invention further provides for "on-demand" controlled release of active agents, which include biologically active agents such as therapeutic drugs, vitamins, antimicrobials, contraceptive agents, pesticides, fungicides, flavors, fragrances, and the like.

There are a number of problems that should be addressed when designing or choosing trans-dermal delivery systems. These include isolation of the drug, or other active substance to be delivered transdermally, from an incompatible adhesive matrix. It is necessary to effect the partitioning of the active substance into the skin from the adhesive matrix of a monolithic transdermal patch. It is necessary to overcome unwanted plasticization of a transdermal patch associated with chemical enhancers and liquid drugs and other active substances. It is desirable to improve storage stability of a drug or other active substance in the matrix of the transdermal patch. It would be desirable to be able to deliver a drug or other active substance on command or "as needed."

According to the present invention, a transdermal delivery system uses an external matrix or vehicle, and microcapsules which contain a drug, pharmaceutical substance, or other substance to be delivered. The substance to be delivered would therefore be an "active substance." The active substance to be delivered is released from the microcapsules by the application of energy such as ultrasonic energy. This allows the active substance to be released into the external matrix or vehicle in a controlled manner and allows the selection of a stable environment for the active substance in the microcapsules prior to use.

In one particular embodiment of the invention, the application of energy is accomplished at least in part by the application of ultrasonic energy at a resonant frequency matched to the microcapsules.

In one particular embodiment of the invention, a delivery-enhancing substance is included in the microcapsules with the active substance to be delivered. In another particular embodiment of the invention, a delivery-enhancing substance is separately contained in different microcapsules, and in yet another embodiment of the invention, a delivery-enhancing substance is contained within the external matrix or vehicle.

In accordance with one optional aspect of the invention, the external matrix or vehicle is chosen to have a solubility parameter which favors transdermal delivery of the active substance to be delivered across the dermal layers. The difference between the solubility parameters of the drug or other substance to be delivered transdermally and the skin is made small in comparison to the difference between the solubility parameters of the drug or other substance to be delivered transdermally and the external matrix or vehicle. This enhances the transdermal flux of the drug or other active substance.

According to the present invention, the transdermal device is activated by ultrasound or heat. In an exemplary embodiment of the present invention, a device equipped with multi-source element providing ultrasound radiation or heat does the activation of the drug or other active substance to be delivered transdermally from the microcapsules.

According to another optional aspect of the present invention, a transdermal patch is constructed with the outer disc and inner disc. The inner disc contains the encapsulated agents in the microspheres, while the outer disc provides the means of attaching the patch to the skin, assuring excellent contact of the inner disc with skin surface.

According to another aspect of the present invention, the rate of the drug release from the patch and its transdermal flux are controlled in a precise manner by the application of energy.

In another exemplary embodiment, therapeutic agent includes the following:
(1) peptides such as melanin concentrating hormone, melanin stimulating hormone, trypsin inhibitor, Bowman Burk inhibitor, luteinizing hormone releasing hormone, bombesin, cholecystokinin, insulin, gastrin, endorphins, enkephalins, growth hormone, prolactin, oxytocin, follicle stimulating hormone, human chorionic gonadotropin, corticotropin, β-lipotropin, .γ-lipotropin, calcitonin, glucagon, thyrotropin, elastin, cyclosporin, and collagen;
(2) monoclonal antibodies;
(3) factors such as hyaluronic acid, heparin, mad heparin sulfate;
(4) anti-sense peptides and anti-sense oligonucleotides such as an antisense oligonucleotide capable of binding the DNA encoding at least a portion of Ras, an antisense oligonucleotide capable of binding the DNA encoding at least a portion of basic fibroblast growth factor, and the anti-sense ras/p53 peptide;
(5) immunosuppressants and anti-inflammatory agents;
(6) chelants and chelating agents such as penicillamine, citrate, ascorbate, diethylenetriaminepentaacetic acid, dihydroxypropylethylenediamine, cyclohexanediaminetetraacetic acid, ethylenediaminetetraacetic acid, ethylene glycol-bis(.beta.-aminoethyl ether)N,N,N',N',-tetraacetic acid, etidronic acid, dimethylsulfoxide, dipyridoxylethylenediaminediacetate-bisphosphate, N,N'-(1,2-ethanediyl-bis(oxy-2,1-phenylene))bis(N-(carboxymethyl), aminophenoltriacetic acid, tetrakis(2-pyridylmethyl) ethylenediamine, cyanins, and salts thereof; and
(7) DNA encoding at least a portion of the following genes: HLA, dystrophin, CFTR, interleukin-2, tumor necrosis factor, adenosine deaminase, HDL receptor, thymidine kinase,HLA-B7, interleukin-4, melanocyte-hormone gene.
(8) Pain-killers: morphine, fentanyl.

In yet in another exemplary embodiment, the cosmetic agent includes Vitamin A, Vitamin C, Vitamin D, Vitamin E, Vitamin K, beta carotene, collagen, elastin, retinoic acid, aloe vera, lanolin, hyaluronic acid, and nucleosides; a sunscreen agent, said sunscreen agent such as 5% isobutyl-p-aminobenzoate, 5% diallyl trioleate, 2.5% monoglyceryl p-aminobenzoate, 4% propylene glycol p-aminobenzoate, and a composition comprising 2% benzyl salicylate and 2% benzyl cinnamate; a cosmetic cream, ointment, lotion, skin softener, gel, blush, eye-liner, mascara, acne-medication, cold cream, cleansing cream, or oleaginous foam.

In another exemplary embodiment, the composition or more compounds selected from the following:
(1) bacteriostatic agents such as benzalkonium chloride, benzethonium chloride, benzoic acid, benzyl alcohol, butylparaben, cetylpyridinium chloride, chlorobutanol, chlorocresol, methylparaben, phenol, potassium benzoate, potassium sorbate, sodium benzoate and sorbic acid;
(2) antioxidants such as tocopherol, ascorbic acid and ascorbyl palmitate;
(3) preservatives such as essential oils;
(4) buffers and neutralizers;
(5) moisture content control agents and humectants;
(6) ointment bases such as lanolin, lanolin anhydrous, hydrophilic ointment, white ointment, yellow ointment, polyethylene glycol ointment, petrolatum, hydrophilic petrolatum, white petrolatum, rose water ointment, and squalene;
(7) suspending and viscosity-increasing agents such as acacia, agar, alginic acid, aluminum monostearate, bentonite, purified bentonite, magma bentonite, carbomer 934P, carboxymethylcellulose calcium, carboxymethylcellulose sodium 12, carboxymethylcellulose sodium, carrageenan, microcrystalline cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, silicon dioxide, zinc oxide, sodium alginate tragacanth, and xanthan gum;
(8) skin absorption enhancing agents such as pyrrolidones, fatty acids, sulfoxides, amines, terpenes, terpenoids, surfactants, alcohols, urea, glycols, azone, n-alkanols, n-alkanes, orgelase, and alphaderm cream;
(9) bases such as glycerol, propylene glycol, isopropyl myristate, urea in propylene glycol, ethanol and water, and polyethylene glycol;
(10) other agents such as glycerin, hexylene glycol, sorbitol, propylene glycol, and calcium silicate;
(11) oleaginous vehicles;
(12) coloring agents; and
(13) foaming agents.

Overview

The present invention is useful for delivery of drugs, medications, cosmetic substances and other materials through at least one epidermal layer. For the purposes of describing delivery of active substances, the terminology "drug delivery" will be used. Unless a specific active substance is stated, "drug delivery" is intended to describe delivery of any substance for which transdermal or subdermal delivery is to be effectuated. The desired active substance may include, but is not limited to, drugs, other medications, cosmetic substances, nutrients, and tracer substances.

For purposes of this invention, "drug carrier matrix" is intended to include an external matrix, external vehicle or external carrier, meaning that the material is external to microcapsules which hold at least one active substance for delivery prior to use. The drug carrier matrix or vehicle may itself contain additional active substances to be delivered. It is also anticipated that the external matrix or vehicle may optionally contain delivery-enhancing substances.

By "microcapsules", it is meant microcapsules, microparticles, microspheres, liposomes, or combinations thereof, and the like, which are capable of being ruptured by applied energy. Examples of such applied energy would be ultrasonic energy or heat energy as described in the exemplary embodiments. Examples of microcapsules which may be used in embodiments of the present invention can be obtained from Particle and Coating Technologies, Inc., S1. Louis, Mo. Another source is ImaRX Therapeutics, Inc, Tucson, Ariz. The microcapsule can be as described in U.S. Pat. No. 5,733,572. It is also possible to use biocompatible lipid liposomes such as are available from OctoPlus, Leiden, The Netherlands.

While "external matrix or vehicle" refers to a substance in which microcapsules are suspended, it is to be understood that the microcapsules themselves may also include inactive carriers or vehicles as well as the active substance to be delivered.

The present invention provides a transdermal patch system, which includes a patch for the delivery of drugs and biologically active agents by transdermal administration. A patch constructed in accordance with the invention includes active agents. The active agents, as used in one embodiment of the invention, consist essentially of at least 15% by weight of an active substance having a molecular weight between 50 and 25,000 Daltons, a polymer such as polyvinylpyrrolidone, the weight of said polymer being between 7 to 35% by weight of the active substance, and an optional gelling agent, being between 0 and 20% by volume of the system in which the active substance is encapsulated in microspheres.

The present invention further includes a novel method for the delivery of active substance from microcapsules embedded in a monolithic matrix, via their activation by the rupturing of the microcapsules upon application of ultrasound at a resonant frequency at a preferred frequency, or upon application of an amount of heat sufficient to melt or otherwise rupture the microcapsules. A preferred frequency is between 0.1 and 20 MHz, and a more preferred frequency range is between 0.1 and 5 MHz. It is nevertheless anticipated that different frequencies may be useful, depending on the resonance of the microcapsules and the materials used for the microcapsules, active substance and the monolithic matrix. Such useful frequencies would be within a range of 0.1 and 100 MHz. It is to be appreciated that microcapsules having different resonant frequencies may be provided in a single matrix in order to provide staged release of the agent, or to provide selective release of different agents, e.g. by providing ultra-sonic energy at one frequency at a first activation and by providing ultra-sonic energy at a second frequency at a second activation. Another approach is to provide in a single matrix microcapsules which rupture at a predetermined ultrasonic frequency and different microcapsules which do not rupture at that frequency but would rupture when heated. Staged delivery of their contents is provided by applying ultrasound and heat at selected time periods.

The inventive patch is desirably suitable for "on-demand" controlled release of active substances which include biologically active agents such as therapeutic drugs, vitamins, antimicrobials, contraceptive agents, pesticides, insect repellants, fungicides, flavors, fragrances, or the like.

In one aspect, the present invention provides a transdermal patch in which the dispersed drug or other active substance to be delivered transdermally is activated (released) on demand by the patient.

A first feature of the present invention is that a drug or other active substance to be delivered transdermally may thereby be isolated from its incompatible adhesive matrix. This feature of the present invention overcomes shortcomings of existing conventional transdermal patches by dissolving or formulating the drug or other active substance to be delivered transdermally in a compatible pharmaceutically-acceptable solvent or excipient vehicle, and then encapsulating the drug solution or formulation in microcapsules, microparticles, microspheres, or combinations thereof, and the like. The drug-containing microcapsules, and the like, are suspended in a suitable composition, such as pressure-sensitive adhesive, adhesive hydrogel, cream and the like, which contains a permeation-enhancing agent and serves as an outer solvent in which the drug-containing microcapsules are suspended. In such a storage and delivery means, the microcapsules, for example, are made of a substance or material that does not permit diffusion into or out of the microcapsule and does not allow leaching out of its contents to any significant extent. However, the microcapsules are capable of being ruptured, broken, split or melted down by using either ultrasound of resonance energy or heat energy. This allows the drug or other active substance to be delivered transdermally to be released from the ruptured, broken, split or melted microcapsules and permits the mixing of released active substance with the matrix containing permeation enhancer. Accordingly, a mixture and combination of active drug and permeation enhancer in a base composition as desired are provided to the user at the site of application.

A second feature of the present invention is the improved partitioning of the drug, or other active substance to be delivered transdermally, into the skin from the adhesive matrix of the monolithic transdermal patch. Partitioning of the drug or other active substance to be delivered transdermally into skin is dependent on the difference in the chemical potentials of the drug or other active substance to be delivered transdermally in the external matrix or vehicle and the skin. The driving force of the drug or other active substance to be delivered transdermally from the external matrix or vehicle to the skin is directly proportional to the difference of the solubility parameter between the drug or other active substance to be delivered transdermally and the external matrix or vehicle. The smaller the difference between the solubility parameters of the drug or other active substance to be delivered transdermally and the skin in comparison to the difference between the solubility parameters of the drug or other active substance to be delivered transdermally and the drug-carrying matrix, the greater the transdermal flux. Therefore, transdermal delivery of lipophilic drugs is most effective from hydrogel matrices; and vice versa, transdermal delivery of hydrophilic drugs such as e.g., HCl salts of amine drugs is most effective from lipophilic matrices.

A third feature of the present invention is the ability to eliminate unwanted plasticization of a transdermal patch associated with chemical enhancers and liquid drugs. Encapsulation of the drugs and enhancers prohibits any interaction with an adhesive or non-adhesive external matrix or vehicle until their release upon activation "on demand" when patch is affixed to the skin.

A fourth feature of the present invention is the possibility of improved storage stability of a drug or other active substance to be delivered transdermally in the matrix of the transdermal patch. The transdermal patch of the present invention is manufactured in a pre-activated state for reasons of storage stability, manufacture safety, user safety, or control of release characteristic considerations. Drugs or active agents such as insulin or Vitamin C that are unstable in aqueous solution and easy oxidizable lend themselves to be encapsulated and activated in the external matrix or vehicle on demand using resonance ultrasound or heat.

A fifth feature of the present invention is the possibility of activating the patch "on demand," e.g. by a patient. The transdermal drug delivery system of the present invention may desirably be activated by a patient (or other person applying the system to the patient). This may be performed just prior to or immediately after applying the system to the patient's skin. It may thereafter be performed as needed.

The active substance may be any of a variety of medicinal or beneficial agents. Examples include anti-fungal agents, hormones, vitamins, peptides, enzymes, anti-allergic agents, anti-coagulation agents, antituberculars, antivirals, antibiotics, antibacterials, anti-inflammatory agents, antiprotozoans, local anesthetics, growth factors, cardiovascular agents, diuretics, and radioactive compounds; selegiline, scopolamine, nicotine, methylnicotinate, mechlorisone dibutyrate, naloxone, methanol, caffeine, salicylic acid, and 4-cyanophenol; anti-fungal agents such as ketoconazole, nystatin, griseofulvin, flucytosine, miconazole, and amphotericin B; hormones such as growth hormone, melanocyte stimulating hormone, estradiol, progesterone, testosterone, beclomethasone dipropionate, betamethasone, betamethasone acetate and betamethasone sodium phosphate, betamethasone disodium phosphate, betamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide and fluorocortisone acetate; vitamins such as cyanocobalamin neinoic acid, retinoids, retinol palmitate, ascorbic acid, and .alpha.-tocopherol, B-12 and other vitamins; peptides and enzymes such as manganese super oxide dismutase and alkaline phosphatase; the anti-allergic agent is amelexanox; the anti-coagulation agents such as phenprocoumon and heparin; the antituberculars such as paraminosalicylic acid, isoniazid, capreomycin sulfate cycloserine, ethambutol hydrochloride ethionamnide, pyrazinamide, rifampin, and streptomycin sulfate; the antivirals such as acyclovir, amantadine azidothymidine, ribavirin and vidarabine monohydrate; the antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin rifampin and tetracycline; the antiinflammatories such as diflunisal, ibuprofen, indomethacin, meclofenamate, mefenamic acid, naproxen, oxyphenbutazone, phenylbutazone, piroxicam, diclofenac, sulindac, tolmetin, aspirin and salicylates; the antiprotozoans such as chloroquine, hydroxychloroquine, metronidazole, quinine and meglumine antimonate; the local anesthetics such as bupivacaine hydrochloride, chloroprocaine hydrochloride, etidocaine hydrochloride, lidocaine, mepivacaine hydrochloride, procaine hydrochloride and tetracaine hydrochloride; the growth factors such as Epidermal Growth Factor, acidic Fibroblast Growth Factor, Basic Fibroblast Growth Factor, Insulin-Like Growth Factors, Nerve Growth Factor, Platelet-Derived Growth Factor, Stem Cell Factor, Transforming Growth Factor of the .alpha. family and Transforming Growth Factor of the .beta. family; the cardiovascular agents are such as clonidine, propranolol, lidocaine, nicardipine and nitroglycerin; the diuretics are such as mannitol and urea; and wherein the radioactive particles are such as strontium, iodine, rhenium and yttrium.

In another exemplary embodiment, the therapeutic agent inside of the microcapsules includes one or more of the following:
(1) Peptides such as melanin concentrating hormone, melanin stimulating hormone, trypsin inhibitor, Bowman Burk inhibitor, luteinizing hormone releasing hormone, bombesin, cholecystokinin, insulin, gastrin, endorphins, enkephalins, growth hormone, prolactin, oxytocin, follicle stimulating hormone, human chorionic gonadotropin, corticotropin, P-lipotropin, -lipotropin, calcitonin, glucagon, thyrotropin, elastin, cyclosporin, and collagen;
(2) monoclonal antibodies;
(3) factors such as hyaluronic acid, heparin, mad heparin sulfate;
(4) anti-sense peptides and anti-sense oligonucleotides such as an antisense oligonucleotide capable of binding the DNA encoding at least a portion of Ras, an antisense oligonucleotide capable of binding the DNA encoding at least a portion of basic fibroblast growth factor, and the anti-sense ras/p53 peptide;
(5) immunosuppressants and anti-inflammatory agents;
(6) chelants and chelating agents such as penicillamine, citrate, acerbate, diethylenetriaminepentaacetic acid, dihydroxypropylethylenediamine, cyclohexanediaminetetraacetic acid, ethylenediaminetetraacetic acid, ethylene glycol-bis(.beta. amino ethyl ether)N,N,N,N',-tetraacetic acid, etidronic acid, dimethylsulfoxide, dipyridoxylethylenediaminediacetate-bisphosphate, N,N'-(1,2-ethanediyl-bis(oxy-2,1 phenylene))bis(N-(carboxymethyl), aminophenoltriacetic acid, tetrakis(2-pyridylmethyl) ethylenediamine, cyanins, and salts thereof; and
(7) DNA encoding at least a portion of the following genes: HLA, dystrophin, CFTR, interleukin-2,' tumor necrosis factor, adenosine deaminase, HDL receptor, thymidine kinas, HLA-B7, interleukin-4, melanocyte stimulating hormone gene, and melanin concentrating hormone gene.
(8) Pain-killers like morphine and fentanyl.

In yet another exemplary embodiment, the inventive patch may be used to deliver a cosmetic agent. The cosmetic agent may include Vitamin A, Vitamin C, Vitamin D, Vitamin E, Vitamin K, beta carotene, collagen, elastin, retinoic acid, aloe vera, lanolin, hyaluronic acid, and nucleosides; a sunscreen agent, said sunscreen agent such as 5% isobutyl-p-aminobenzoate, 5% diallyl trioleate, 2.5% monoglyceryl p-aminobenzoate, 4% propylene glycol p-aminobenzoate, and a composition comprising 2% benzyl salicylate and 2% benzyl cinnamate; a cosmetic cream, ointment, lotion, skin softener, gel, blush, eye-liner, mascara, acne-medication, cold cream, cleansing cream, or oleaginous foam.

In another exemplary embodiment, the composition of the microcapsule interior comprises one or more compounds selected from the following:
(1) bacteriostatic agents such as benzalkonium chloride, benzethonium chloride, benzoic acid, benzyl alcohol, butylparaben, cetylpyridinium chloride, chlorobutanol, chlorocresol, methylparaben, phenol, potassium benzoate, potassium sorbate, sodium benzoate and sorbic acid;
(2) antioxidants such as tocopherol, ascorbic acid and ascorbyl palmitate;
(3) preservatives such as parables, quaternary ammonium compounds, alcohols, phenols, and essential oils;
(4) buffers and neutralizers;
(5) moisture content control agents and humectants;
(6) ointment bases such as lanolin, lanolin anhydrous, hydrophilic ointment, white ointment, yellow ointment, polyethylene glycol ointment, petrolatum, hydrophilic petrolatum, white petrolatum, rose water ointment, and squalene;
(7) suspending and viscosity-increasing agents such as acacia, agar, alginic acid, aluminum monostearate, bentonite, purified bentonite, magma bentonite, carbomer 934P, carboxymethylcellulose calcium, carboxymethyl cellulose sodium 12, carboxymethylcellulose sodium, carrageenan, microcrystalline cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, silicon dioxide, zinc oxide, sodium alginate tragacanth, and xanthan gum;
(8) skin absorption enhancing agents such as pyrrolidones, fatty acids, sulfoxides, amines, terpenes, terpenoids, surfactants, alcohols, urea, glycols, azone, n-alkanols, n-alkanes, orgelase, and alphaderm cream;
(9) bases such as glycerol, propylene glycol, isopropyl myristate, urea in propylene glycol, ethanol and water, and polyethylene glycol;
(10) other agents such as glycerin, hexylene glycol, sorbitol, propylene glycol, and calcium silicate;
(11) oleaginous vehicles; (12) coloring agents; and (13) foaming agents.
(12) coloring agents; and
(13) foaming agents The inventive patch particularly lends itself to transdermal drug delivery and for topical application of dermatologic ally acting agents. In addition, the inventive patch is useful for controlled delivery of medications to wounds.

Other examples of active agents that may be suited for delivery by this invention are found in the U.S. Pat. No. 4,830,355.

MODES FOR CARRYING OUT THE INVENTION

To facilitate concise but comprehensive disclosure, each of the references cited herein, including each patent and publication, is incorporated by reference in its entirety to the fullest extent permitted by law, except for any passages that are clearly inconsistent with the description herein.

Patch Construction

Figure 1:
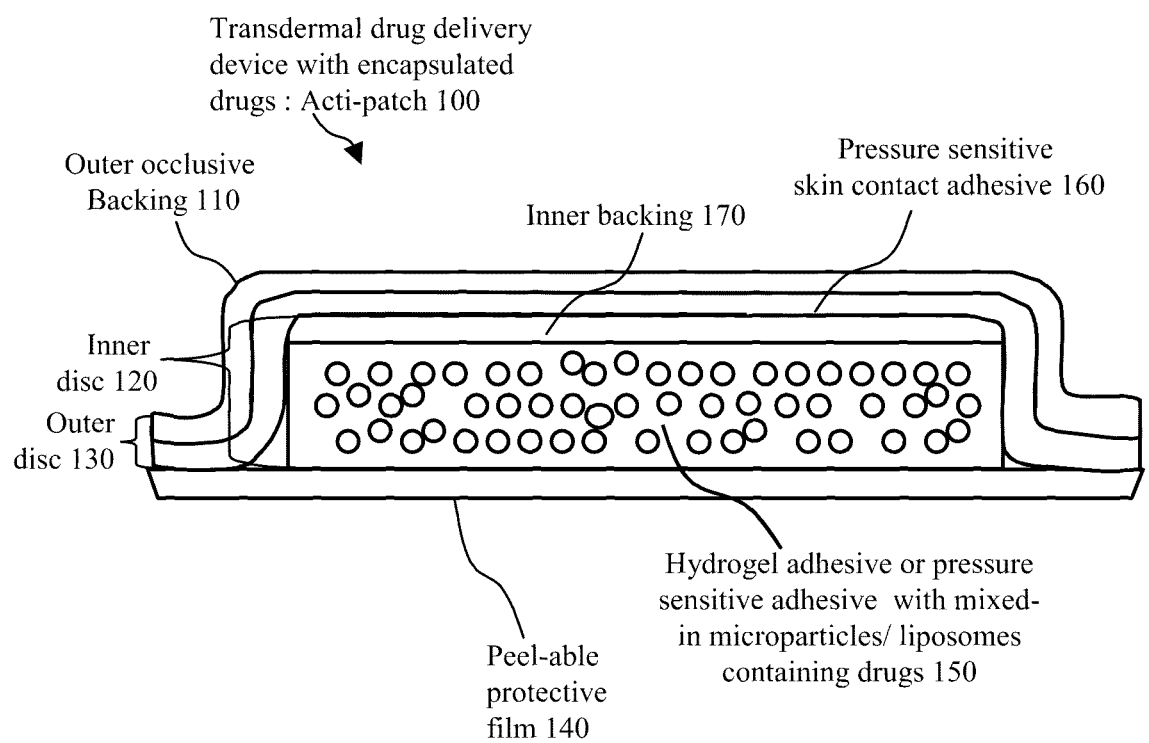
FIG. 1 is a view of a transdermal drug delivery patch constructed according to one embodiment of the invention, using encapsulated agents and multiple layers.

FIG. 1 is a view of a transdermal drug delivery patch constructed according to one embodiment of the invention, using encapsulated agents and multiple layers. FIG. 1 depicts as the transdermal drug delivery patch 100 the first exemplary embodiment of the invention. It has a multiplicity of layers laminated to each other, thereby forming an outer disc 130, an inner disc 120, and a protective peel able release film 140. The inner disc 120 is formed of an inner backing 170 attached to an adhesive layer 150 (e.g. hydrogel adhesive or pressure sensitive adhesive with mixed-in microparticles) and a pressure-sensitive adhesive layer 160. Adhesive layer 150, (and optionally, pressure-sensitive adhesive layer 160) contains dispersed microparticles (e.g. liposomes) with encapsulated drugs. The outer disc 130 is formed of an outer occlusive packing 110, which is attached to the inner disc 120 via the skin-contact pressure-sensitive adhesive 160.

The microcapsules provide a convenient container for the active substance. One example of such a microcapsule is described in the aforementioned U.S. Pat. No. 5,733,572, as microspheres and microbubbles. U.S. Pat. No. 5,733,572 describes micro spheres which may be formed from a biocompatible lipid or polymer. U.S. Pat. No. 5,733,572 describes a variety of materials and precursors for the microcapsules and fill materials for the microcapsules. Alternatively one may construct the microcapsules as described in U.S. Pat. No. 3,242,051, using polyvinyl stearate or another side-chain crystallizable polymer, as a precoating material in a two-step microencapsulation process. Such microcapsules may be made of polymeric shells or liposomes. Another alternative is a gas-containing microcapsule as a drug carrier, which is composed of a soft sheath of a polymer or the like, as reported in Japanese Journal of Applied Physics, 27 (1988) Supplement 27-1, pp. 125-127. In some cases, the microcapsule is made so that application of heat causes the microcapsule wall to melt.

In operation, the peelable protective film 140 is removed and the outer disc 130, with the adhesively attached inner disc 120, is placed on the skin and firmly pressed to assure a very good contact of the inner disc 120 with the surface of the skin.

Figure 2:
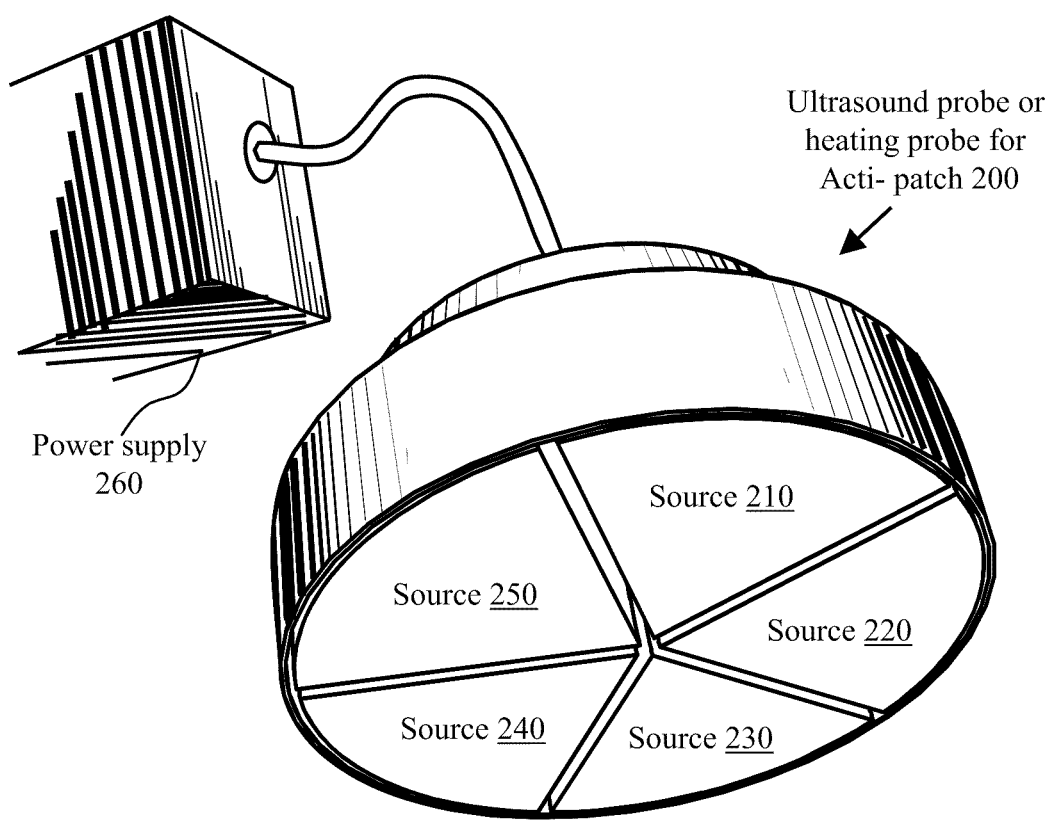
FIG. 2 shows an activating probe for a patch in accordance with one embodiment of the invention.

FIG. 2 shows an activating probe for a patch in accordance with one embodiment of the invention. FIG. 2 depicts an activating probe that has a multiplicity of energy sources 210, 220, 230, 240, 250. The sources are desirably independent from each other. Each energy source may be an ultrasound probes or a heat-generating source.

Patch Activation by Ultrasound Energy

Figure 3:
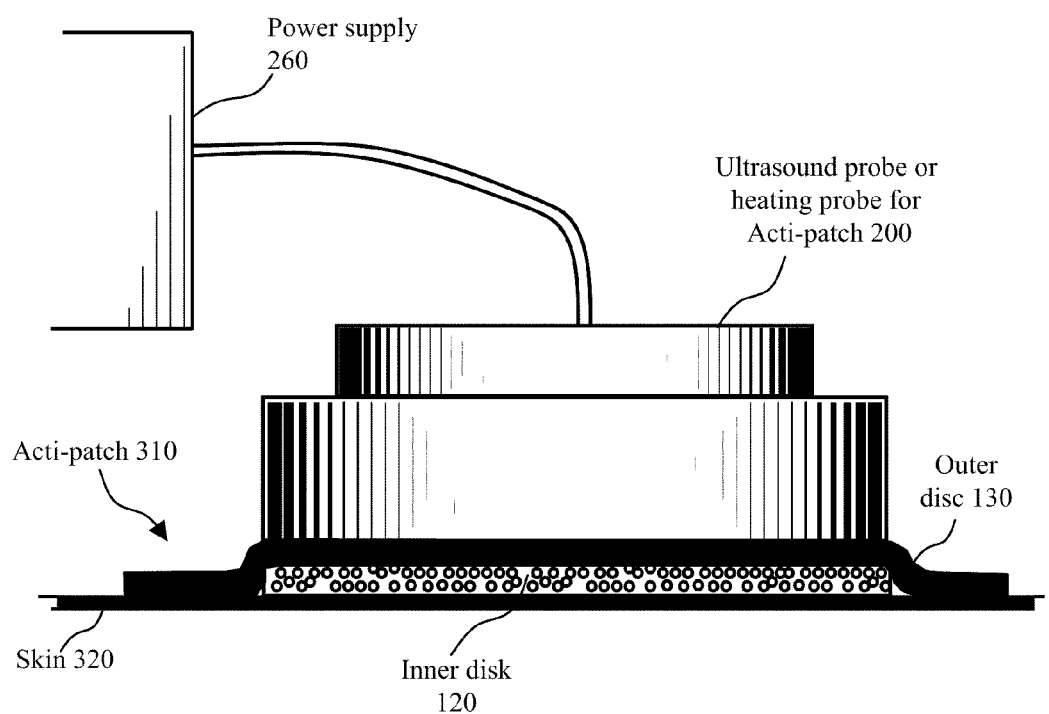
FIG. 3 shows an arrangement of an activating probe and the inventive patch on the user's skin.

In operation, the activating probe is placed on top of a patch 310 of the present invention in contact with the outer disc 130 as depicted by FIG. 3. Ultrasound energy is emitted by the probe 200 having energy supplied by power supply 260 causes some or all of the microspheres to rupture, thereby releasing the encapsulated agent into the matrix of the inner disc 120. Alternatively, or in tandem therewith, heat energy emitted by the probe 200 causes some or all of the microspheres to melt, releasing the encapsulated agents into the matrix of the inner disc 120.

Figure 4:
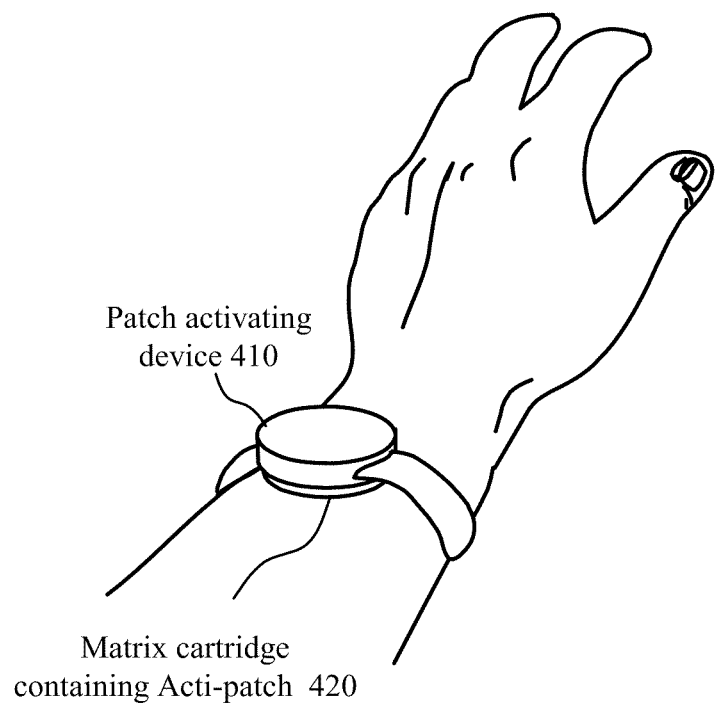
FIG. 4 shows a portable transdermal drug delivery device secured to a user's arm in accordance with an embodiment of the invention.

FIG. 4 shows an arrangement of an activating probe in the form of a patch activating device 410 strapped around the user's wrist above a matrix cartridge 420 containing the inventive patch adhered to the patient's skin. The patch activating device 410 contains a battery and an ultrasonic energy source, permitting patch activation by ultrasound.

In accordance with the present invention, a microcapsule is irradiated with a sound wave having a frequency corresponding to the resonance frequency of the microcapsule, and so the sound energy is efficiently absorbed. This results in the release of the drug or other active substance to be delivered transdermally from the microcapsule upon the rupturing of the microcapsule walls.

The principle is now explained from the theory of sound resonance a gas-containing microcapsule, which is used as a drug carrier and has a resonance frequency corresponding to the surrounding pressure, diameter, and elasticity of the microcapsule film, much like a minute bubble in water. The formula of the resonance frequency of a bubble in water presented by M. Minneart is easy to understand:

$$f = \frac{1}{2\Pi r}(3kP/\gamma)^{1/2}$$

Wherein
f represents a resonance frequency,
r represents the radius of a bubble or a gas-containing microcapsule,
k represents the ratio of the specific heat at a constant pressure and the specific heat volume of a gas, and is a constant of about 1.4 in the case of nitrogen or oxygen,
P represents a pressure applied to a liquid, and
$\gamma$ represents the specific weight of a liquid.

It is clear from this formula that as the pressure P increases, the resonance frequency f becomes high, while as the diameter increases, the resonance frequency becomes low. This formula is a calculated and theoretical formula in the adiabatic state, in which the viscosity of water and the surface tension are disregarded, but it is known that this formula is accurate with respect to measured values. This formula also approximately holds with respect to a gas-containing microcapsule as a drug carrier, which is composed of a soft sheath of a polymer or the like. This is reported in Japanese Journal of Applied Physics, 27 (1988) Supplement 27-1, pp. 125-127, in which the relationship between the resonant frequency and the pressure of a microcapsule in water is discussed.

In order to examine whether or not the stable irradiation of a sound wave having a resonance frequency is possible when the pressure varies, the shift of the resonance frequency is calculated by using the above formula.

For example, when the diameter of the gas-containing microcapsule is 0.003 mm, which is a convenient size for a drug microcapsule used for an ordinary purpose, and the microcapsule is in an aqueous solution having a pressure approximate to atmospheric pressure, the resonance frequency is 2185.78 kHz.

Patch Activation by Heat

Application of heat to the inventive patch causes the microcapsule polymeric wall to melt, thereby releasing the drug or other active substance to be delivered transdermally into the external matrix or vehicle. Effective melting of the microcapsule's polymeric walls is achievable by producing an adiabatic heat flux into the matrix, which generates an high temperature in a very short time using a low voltage discharge of the high-capacity condenser. It is believed that the heat may be external or may include body heat. It is also believed that the effects of ultrasonic energy will impart heat to the microcapsules.

Typical Operation

FIG. 4 shows a portable transdermal drug delivery device constructed in accordance with an embodiment of the invention. This is a portable self-contained battery-operated transdermal drug delivery device with exchangeable patch cartridges constructed in accordance with the invention, containing encapsulated agents in a matrix capable of programmable drug delivery. Its use is by:
1. Placing the inventive patch on the skin.
2. Placing a patch-activating probe on top of the inventive patch.
3. Turning on the probe for a predetermined period of time, during which the microparticles in the inner disc of the inventive patch are destroyed and the encapsulated agent is released into the matrix.
4. The agent migrating in the matrix and being absorbed by the skin on the skin-matrix interphase.

EXAMPLE

An Insulin Patch

Prepare insulin for transdermal delivery by preparing microcapsules filled with the insulin. A sufficient quantity of the microcapsules are provided within a monolithic matrix to provide transcutaneous dosages of the insulin. This can be prepared for a single dose or as multiple partial doses. This is part of a transdermal drug delivery patch, depicted in FIG. 1, using the insulin as the encapsulated agent.

The matrix is fixed to the skin by removing the peelable protective film 140 and applying the patch to the skin. The outer disc 130, with the adhesively attached inner disc 120, is placed on the skin and firmly pressed to assure a very good contact of the inner disc 120 with the surface of the skin. In order to release the insulin for transcutaneous delivery, the activating probe 200 shown in FIG. 2 is used. The energy is at a resonant frequency selected for the microcapsules, such as 2.5 MHz. The user has the choice of applying sufficient energy to release substantially all of the microcapsules, or alternatively may apply sufficient energy to effect a partial release.

As shown in FIG. 2, the multiple energy sources 210, 220, 230, 240, 250 of probe 200 facilitate providing partial doses by causing the application of energy to the patch to be localized. This provides control of the partial dose according to the localized energy applied to the inner disc 120. In the event of a partial release, the user may later apply additional energy at different localized areas of the inner disc 120, thereby releasing additional amounts of the insulin. The multiple energy sources 210, 220, 230, 240, 250 therefore make it convenient to apply the additional energy. Upon the application of the energy, the microcapsules embedded in a monolithic matrix are activated by rupturing upon application of ultrasound at a the resonant frequency. The reader will appreciate that in accordance with the principle described above, heat may alternatively be applied to localized areas of the inner disc 120 to selectively provide in the matrix microcapsules that are selectively rupturable at different frequencies and to tune one or a multiplicity of sources of energy to the respective frequencies as it is desired to dispense the agent. Another alternative is to provide in the matrix some microcapsules that rupture at selected frequencies and some microcapsules that rupture at selected temperatures, and to provide ultrasonic activation at one or more frequencies and heat during a particular sequence of time.

Upon rupture of the walls of the microcapsules, the insulin is released, causing the insulin to disperse through the monolithic matrix, and enters the body transdermally. The insulin is then able to migrate in the matrix and become absorbed through the skin. By providing patient control over time, it is possible to provide a fairly large dose on the assumption that the full dose will not be used absent a perceived need.

This technique allows the patient to activate the patch using transcutaneous ultrasound following meals and in accordance with the patient's blood sugar levels. By using the patch, subcutaneous injections of the insulin or other therapeutic agent can be avoided. The ability to provide multiple dosages allows the user to estimate desired dosages within a predetermined range of dosages. It further allows the dosage to be distributed over a desired time period, and modified according to perceived sugar intake.

The invention claimed is:

1. A portable transdermal drug delivery device consisting of:
   (A) a transdermal patch for infusing active substances into a user's body through the skin comprising:
   an inner disc, the inner disc including (i) encapsulated agents in microcapsules, wherein the microcapsules retain the encapsulated agents prior to activation by energy capable of rupturing the microcapsules and (ii) an external matrix or vehicle; and an outer disc for attachment of the patch to the skin of the user, thereby facilitating contact of the inner disc with a surface of the skin;
   (B) an activating probe attached to said transdermal patch and being equipped with a single multi-source element, wherein said multi-source element is comprised of multiple energy sources for providing ultrasound radiation or heat energy at different localized areas of said inner disc,
   wherein said activating probe is adapted for activating the transdermal patch by rupturing the microcapsules, thereby releasing said encapsulated agents into the external matrix or vehicle of the inner disc of said transdermal patch; and
   (C) a power supply for supplying energy to said multi-source element.

2. The portable transdermal drug delivery device of claim 1 wherein the active substance to be infused is a pharmaceutical substance and the pharmaceutical substance is retained prior to infusion in a compatible pharmaceutically-acceptable solvent or excipient vehicle, encapsulated in the microcapsules.

3. The portable transdermal drug delivery device of claim 2 wherein the microcapsules are suspended in said external matrix or vehicle, selected from the group consisting of pressure-sensitive adhesives, adhesive hydrogels, creams, and combinations thereof, which contains a permeation-enhancing agent and serves as an outer solvent in which the microcapsules are suspended.

4. The portable transdermal delivery device of claim 2 wherein the microcapsules are suspended in an external matrix or vehicle, selected from the group consisting of pressure-sensitive adhesives, adhesive hydrogels, creams, and combinations thereof, which contains a permeation-enhancing agent and serves as an outer solvent in which the microcapsules are suspended, and the microcapsules are made of a material that is capable of being ruptured, broken, split, or melted down at a resonance frequency between 0.1 and 100 MHz allowing the contents to be released into the external matrix or vehicle.

5. The portable transdermal delivery device of claim 1 wherein the inner disc includes encapsulated agents in microspheres dispersed in a hydrogel adhesive.

6. The portable transdermal delivery device of claim 1 wherein the inner disc includes encapsulated agents in microspheres dispersed in a pressure-sensitive adhesive.

7. The portable transdermal delivery device of claim 1 wherein the inner disc includes encapsulated agents in microspheres dispersed in an aqueous medium in a patch.

8. The portable transdermal delivery device of claim 1 wherein the microspheres have sizes between 0.01 and 100 micrometers.

9. The portable transdermal delivery device of claim 1 wherein the microspheres include polymeric shells.

10. The portable transdermal delivery device of claim 1 wherein the microspheres are made of liposomes.

11. The portable transdermal delivery device of claim 1 wherein the inner disc includes at least one of drug, biologically active compound, excipient, or skin permeation enhancer.

12. The portable transdermal delivery device of claim 1, wherein said active substances include insulin provided for transdermal delivery.

13. The portable transdermal delivery device of claim 1, wherein said active substances include a vitamin.

14. The portable transdermal delivery device of claim 1, wherein said active substances include a skin permeation enhancer.

15. The portable transdermal delivery device of claim 1, wherein the external matrix or vehicle holding the microcapsules includes skin permeation enhancer.

* * * * *